United States Patent [19]

Orwick et al.

[11] Patent Number: 4,957,536

[45] Date of Patent: Sep. 18, 1990

[54] METHOD FOR INCREASING AXILLARY BRANCHING, TILLERING, FLOWERING AND YIELD OF AGRONOMIC AND HORTICULTURAL CROPS WITH CERTAIN 2-(2-IMIDAZOLIN-2-YL)-PYRIDINES AND QUINOLINES

[75] Inventors: Philip L. Orwick, Yardley, Pa.; Andrew R. Templeton, West Trenton, N.J.

[73] Assignee: American Cyanamid Company, Stamford, Conn.

[21] Appl. No.: 249,243

[22] Filed: Sep. 22, 1988

Related U.S. Application Data

[63] Continuation of Ser. No. 910,319, Sep. 22, 1986, abandoned, which is a continuation of Ser. No. 635,787, Jul. 30, 1984, abandoned, which is a continuation-in-part of Ser. No. 490,548, May 6, 1983, abandoned, which is a continuation-in-part of Ser. No. 255,012, Apr. 17, 1981, abandoned, which is a continuation-in-part of Ser. No. 155,866, Jun. 2, 1980, abandoned.

[51] Int. Cl.$^5$ .................... A01N 43/48; A01N 43/64; A01N 57/00; A01N 57/10

[52] U.S. Cl. ............................................ 71/92; 71/86; 71/87

[58] Field of Search .................. 71/72, 92, 94

[56] References Cited

U.S. PATENT DOCUMENTS

| | | | |
|---|---|---|---|
| 3,495,969 | 2/1970 | Driscoll | 71/92 |
| 4,029,492 | 6/1977 | Cross et al. | 71/92 |
| 4,188,487 | 2/1980 | Los | 71/92 |
| 4,201,565 | 5/1980 | O'Neal | 71/76 |
| 4,404,012 | 9/1983 | Orwick et al. | 71/92 |

*Primary Examiner*—Richard L. Raymond
*Assistant Examiner*—B. Bembenick
*Attorney, Agent, or Firm*—Alice C. Brennan

[57] ABSTRACT

There is provided a method for increasing axillary branching, tillering, flowering, and yield of agronomic and horticultural crops, by applying to said crop plants or to soil containing the seeds or other propagating organs of said plants, an effective amount of a 2-(2-imidazolin-2-yl)pyridine or 2-(2-imidazolin-2-yl)quinoline derivative.

9 Claims, No Drawings

METHOD FOR INCREASING AXILLARY BRANCHING, TILLERING, FLOWERING AND YIELD OF AGRONOMIC AND HORTICULTURAL CROPS WITH CERTAIN 2-(2-IMIDAZOLIN-2-YL)-PYRIDINES AND QUINOLINES

This application is a continuation of application Ser. No. 06/910,319 filed Sept. 22, 1986, abandoned, which is a continuation of Ser. No. 06/635,787, filed July 30, 1984, abandoned, which is a continuation-in-part of Ser. No. 06/490,548, filed May 6, 1983, abandoned, which is a continuation-in-part of Ser. No. 06/255,012, filed Apr. 17, 1981, abandoned, which is a continuation-in-part of Ser. No. 06/155,866, filed June 2, 1980, abandoned.

This invention relates to a method for increasing axillary branching, tillering, flowering and yield of agronomic and horticultural crops by applying to the foliage of said crops or to soil containing seeds or other propagating organs thereof, an axillary branching, tillering, flowering or yield increasing amount of a compound having the structure:

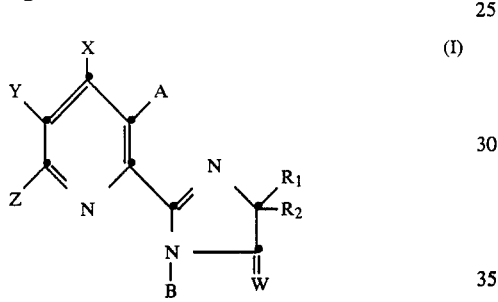

(I)

wherein $R_1$ is $C_1$-$C_4$ alkyl;

$R_2$ is $C_1$-$C_4$ alkyl or $C_3$-$C_6$ cycloalkyl; and when $R_1$ and $R_2$ are taken together they may represent $C_3$-$C_6$ cycloalkyl optionally substituted with methyl;

A is $COOR_3$, $CONHR_6$, CHO, $CH_2OH$, $COCH_3$, $COC_6H_5$, CN, $CH_3$, CH=NOH, $CH_2COOH$, CONHOH, $CH_2CH_2COOH$, $CHR_8OH$,

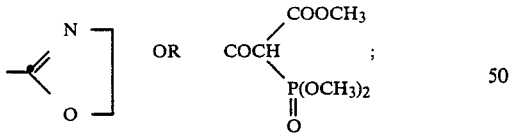

$R_3$ is hydrogen,

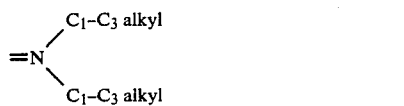

$C_1$-$C_{12}$ alkyl optionally substituted with one of the following groups: $C_1$-$C_3$ alkoxy, halogen, hydroxyl, $C_3$-$C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium;

$C_3$-$C_{12}$ alkenyl optionally substituted with one of the following groups: $C_1$-$C_3$ alkoxy, phenyl, halogen or loweralkoxycarbonyl or with two $C_1$-$C_3$ alkoxy groups or two halogen groups;

$C_3$-$C_6$ cycloalkyl optionally substituted with one or two $C_1$-$C_3$ alkyl groups;

$C_3$-$C_{10}$ alkynyl optionally substituted with one or two $C_1$-$C_3$ alkyl groups; or, A cation, as for example, alkali metals, alkaline earth metals, manganese, copper, iron, zinc, cobalt, lead, silver, nickel, ammonium and organic ammonium;

$R_6$ is hydrogen, hydroxyl, $C_3$-alkenyl, $C_3$-alkynyl or $C_1$-$C_4$ alkyl optionally substituted with one hydroxyl or one chlorine group;

B is H, $COR_4$ or $SO_2R_5$, provided that when B is $COR_4$ or $SO_2R_5$; A is $COOR_3$ in which $R_3$ is other than H, or a salt-forming cation, $CH_3$ or CN; W is O; and Y and Z are not alkylamino, hydroxyl, or hydroxyloweralkyl;

$R_4$ is $C_1$-$C_{11}$ alkyl, chloromethyl or phenyl optionally substituted with one chloro, one nitro or one methoxy group;

$R_5$ is $C_1$-$C_4$ alkyl or phenyl optionally substituted with one methyl group;

W is O or S;

$R_8$ is $C_1$-$C_4$-alkyl or phenyl;

X is hydrogen, halogen, hydroxyl or methyl, with the proviso that when Y and Z are taken together to form a ring and YZ is represented by the structure: —$(CH_2)_n$—, where n is 3 or 4, X is hydrogen;

Y and Z each represent members selected from the group consisting of hydrogen, halogen, $C_1$-$C_6$ alkyl, hydroxy-loweralkyl, $C_1$-$C_6$ alkoxy, $C_1$-$C_4$ alkylthio, phenoxy, $C_1$-$C_4$-haloalkyl, nitro, cyano, $C_1$-$C_4$ alkylamino, diloweralkylamino or $C_1$-$C_4$ alkylsulfonyl group, or phenyl optionally substituted with one $C_1$-$C_4$ alkyl, $C_1$-$C_4$ alkoxy or halogen; and, when taken together, Y and Z may form a ring in which YZ are represented by the structure: —$(CH_2)_n$, where n is an integer selected from 3 and 4, provided that X is hydrogen;

or 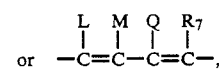

where L, M, Q and $R_7$ each represent members selected from the group consisting of hydrogen, halogen, $C_1C_4$ alkyl, $C_1C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $C_1$-$C_4$ alkylamino, diloweralkylamino, chlorophenyl, ethylphenyl, or phenoxy substituted with one Cl, $CF_3$, $NO_2$ or $CH_3$ group, with the proviso that only one of L, M, Q or $R_7$, may represent a substituent other than hydrogen, halogen, $C_1$-$C_4$ alkyl or $C_1$-$C_4$-alkoxy.

and when W is O and A is CN, $CH_3$ or $COOR_3$, provided that $R_3$ cannot be unsaturated alkyl and Y and Z cannot be alkylamino, dialkylamino or alkylthio, and the N-oxides thereof, and when $R_1$ and $R_2$ are not the same, the optical isomers thereof, and, except when $R_3$ is a salt-forming cation, the acid addition salts thereof.

This invention also relates to a method for effectively inducing and/or accelerating the maturation of cereal crops by applying to the foliage of cereal plants and/or to soil containing seeds of said plants, a maturation accelerating amount of a 2-(2-imidazolin-2-yl)pyridine or 2-(2-imidazolin-2-yl)quinoline compound of formula (I).

Application of the formula (I) 2-(2-imidazolin-2-yl)pyridines or quinolines to the foliage of a variety legumes or herbaceous ornamentals, or to soil in which said plant species are grown, at rates between about 0.0001 kg/ha and 0.01 kg/ha, also has the advantage that such treatment frequently induces a mild dwarfing effect on the treated plants. This dwarfing effect is particularly advantageous in the treatment of ornamental plants wherein the aesthetic value of the plants can be measurably improved by reducing their height and increasing their canopy.

A preferred group of 2-(2-imidazolin-2-yl)-pyridine compounds for use in the methods of the present invention has the formula shown as formula (I) above, wherein $R_1$ is methyl; $R_2$ is methyl, ethyl, isopropyl or cyclopropyl; W is oxygen; B is hydrogen, CO-alkyl $C_1$-$C_6$ or CO-phenyl optionally substituted with chloro, nitro or methoxy; A is $COOR_3$, $CH_2OH$ or CHO where $R_3$ is as described in formula (I) above, X is hydrogen, Y and Z are each selected from the group consisting of hydrogen, $C_1$-$C_6$ alkyl, $C_1$-$C_6$ alkoxy, halo, phenyl, nitro, cyano, trifluoromethyl or methylsulfonyl; and when Y and Z are taken together, YZ is —$(CH_2)_4$.

A more preferred group of these 2-(2-imidazolin-2-yl)pyridines may be illustrated by the formula (Ia):

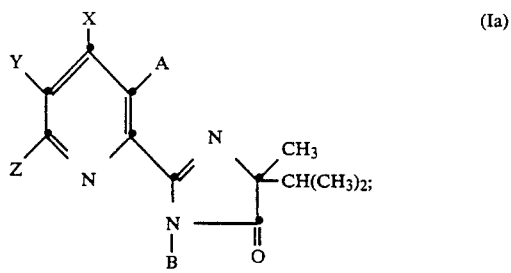

wherein B is hydrogen, CO-alkyl $C_1$-$C_6$ or CO-phenyl; A is $COOR_3$ where $R_3$ is as described in formula (I) above; X is hydrogen and Y and Z each represent hydrogen, $C_1$-$C_6$ alkyl, $C_1$-$C_4$-alkoxy, halo, $C_1$-$C_4$-haloalkyl, or phenyl and, when taken together, YZ represent —$(CH_2)_4$—.

The most preferred formula (Ia), 2-(2-imidazolin-2-yl)pyridine compounds are those wherein B, X, Y and Z are each hydrogen; A is $COOR_3$ and $R_3$ is as described in formula (I) above.

A preferred group of 2-(2-imidazolin-2-yl)-quinoline compounds useful in the methods of the present invention is illustrated by formula (II) below:

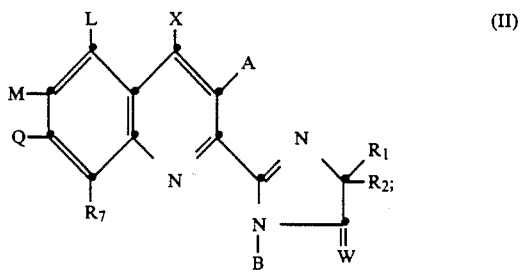

wherein $R_1$, $R_2$, W, B, A, X, L, M, Q and $R_7$ are as defined in reference to formula (I) above, but especially those wherein $R_1$ is methyl; $R_2$ is methyl, ethyl, isopropyl or cyclopropyl; W is oxygen; B is hydrogen, CO-alkyl $C_1$-$C_6$, CO-phenyl optionally substituted with one chloro, nitro or methoxy group; A is $COOR_3$, $CH_2OH$ or CHO; $R_3$ is as defined in formula (I); X is hydrogen and L, M, Q and $R_7$ are each selected from the group consisting of hydrogen, halogen, methoxy, nitro, alkyl $C_1$-$C_4$, $CF_3$, CN, $N(CH_3)_2$, $NH_2$, $SCH_3$, or $SO_2CH_3$, provided that only one of L, M, Q or $R_7$ may be nitro, $CF_3$, CN, $N(CH_3)_2$, $NH_2$, $SCH_3$ or $SO_2CH_3$.

A more preferred group of formula (II) 2-(2-imidazolin-2-yl)quinoline compounds are those wherein X, L and $R_7$ are each hydrogen; $R_1$ is methyl; $R_2$ is methyl, ethyl, isopropyl or cyclopropyl; B is hydrogen or $COCH_3$; A is $COOR_3$, $CH_2OH$ or CHO and $R_3$ is as defined in formula (I); W is oxygen and M and Q each represent a member selected from hydrogen, halogen, methyl, methoxy, nitro, $CF_3$, CN, $N(CH_3)_2$, $NH_2$, $SCH_3$ or $SO_2CH_3$, provided that only one of M or Q may be a substituent other than hydrogen, halogen, methyl or methoxy.

A still more preferred group of formula (II) 2-(2-imidazolin-2-yl)quinolines are those in which $R_1$ is methyl; $R_2$ is isopropyl; W is oxygen; B, X, L, M, Q and $R_7$ are hydrogen; A is $COOR_3$ where $R_3$ is $C_1$-$C_8$ alkyl, hydrogen, $C_3$-$C_8$ alkenyl, $C_3$-$C_8$ alkynyl, $C_3$-$C_6$ cycloalkyl or a cation selected from alkali metals, alkaline earth metals, manganese, copper, iron, zinc, cobalt, lead, silver, nickel, ammonium and aliphatic ammonium.

In formulas (I), (Ia), and (II) above, alkali metals include: sodium, potassium and lithium, but sodium is generally preferred. Further, the term "organic ammonium," is defined as a group consisting of a positively charged nitrogen atom joined to from one to four aliphatic groups, each containing from one to 20 carbon atoms. Among the organic ammonium groups which are illustrative for the preparation of the aliphatic ammonium salts of the formula (I) imidazolinyl nicotinic acids and esters herein are: monoalkylammonium, dialkylammonium, trialkylammonium, tetraalkylammonium, monoalkenylammonium, dialkenylammonium, trialkenylammonium, monoalkynylammonium, dialkynylammonium, trialkynylammonium, monoalkanolammonium, dialkanolammonium, trialkanolammonium, $C_5$-$C_6$-cycloalkylammonium, piperidinium, morpholinium, pyrrolidinium, benzylammonium and equivalents thereof. Exemplary of halogen hereinabove are chlorine, fluorine, bromine, and iodine, but chlorine and bromine are preferred.

The formula (I) 2-(2-imidazolin-2-yl)pyridine and quinoline compounds and methods for their preparation are disclosed in co-pending application for U.S. Letters Patent of Marinus Los, Ser. No. 382,041, filed May 25, 1982, U.S. Pat. No. 4,638,068 and EPO Application No. 811036383, published Dec. 16, 1981, incorporated herein by reference thereto.

The formula (I) 2-(2-imidazolin-2-yl)pyridine and quinoline compounds as hereinabove defined are surprisingly effective for inducing and/or accelerating the maturation of cereal crops and for increasing axillary branching, tillering, flowering and yield of agronomic and horticultural crops by applying to the foliage of said crops or to soil containing seeds or other propagating organs thereof, an amount of active ingredient effective for increasing axillary branching, tillering, flowering or yield, or inducing and/or accelerating maturation of said crops.

It has now been established that some of the formula (I) 2-(2-imidazolin-2-yl)pyridine and quinoline compounds are highly effective for increasing the yield of cotton by applying to the foliage of cotton plants or to soil containing seeds or other propagating organs thereof, a yield enhancing amount, preferably from 1 g/ha to about 380 g/ha, of the formula (1) pyridine or quinoline.

Notably, it has been further established that the above-said formula (I) 2-(2-imidazolin-2-yl)pyridine and quinoline compounds are likewise, very effective for inducing tillering of sugarcane, for increasing the total tonnage of millable cane and for increasing the total sugar yield of sugarcane. These results are obtained by applying to the foliage of immature sugarcane which is at a growth stage between growth stage 1 and growth stage 4–5 (stem elongation and pre-maturity) or to soil containing propagating organs thereof, from about 50 g/ha to about 750 g/ha and preferably about 50 g/ha to about 500 g/ha of the formula (I) 2-(2-imidazolin-2-yl)pyridine or quinoline.

Although it has been disclosed in U.S. Pat. No. 4,404,012, issued Sept. 13, 1983, that the 2-(2-imidazolin-2-yl)pyridine and quinoline compounds of formula (I) are effective as chemical ripening agents for sugarcane when applied to mature cane two to four weeks prior to harvest, it was quite unexpected to find that preemergence treatment of propagating organs of sugarcane or early postemergence treatment of sugarcane, would increase (1) the tillering of the cane, (2) the number of millable canes and (3) the total tonnage of cane.

Some of the formula (I) 2-(2-imidazolin-2-yl)pyridine and quinoline compounds as hereinabove defined are surprisingly effective for inducing and/or accelerating the maturation of cereal crops such as wheat, barley, rye, oats, rice, and corn without adversely affecting the quality of seeds and the yields thereof, when applied to said plants and/or to the soil containing the seeds of said plants in amounts of as low as from 0.0001 kg/ha to 0.01 kg/ha and preferably 0.0002 kg/ha to 0.005 kg/ha.

The method of using formula (I) compounds to accelerate and/or induce maturing, and thus allow the earlier than usual harvesting of cereal crops is, or could be, quite important to the users thereof. Thus, for instance, in any given location, the so treated cereal crops may be harvested well ahead of their usual time of harvest, and the land so freed is immediately available for the planting of a second crop which otherwise would not have sufficient time to grow and reach a stage of size suitable to harvest.

Such a method would also make it possible to allow a cereal crop to be harvested on time even though its planting .may have been delayed due to adverse weather conditions.

Furthermore, the use of formula (I) compounds to accelerate the maturing of cereal crops may make possible the planting and harvesting of such crops in certain regions of the world where the growing season is normally of shorter duration than the time needed to allow said crops to mature.

Interestingly, some formula (I) 2-(2-imidazolin-2-yl)pyridines and quinolines, when applied to legumes such as soybeans, beans, pea, and lentils and/or to soil containing the seeds of said plants, in amounts of as low as from about 0.0001 kg/ha to about 0.01 kg/ha and preferably 0.002 kg/ha to 0.005 kg/ha, will improve the axillary branching and tillering of said plants. The thus-treated legumes also show increased flowering, increased pod set, and increased yields.

While some of the formula (I) compounds, as defined above, are also quite effective for inducing branching and increasing flowering of herbaceous ornamentals such as colei, dahlias, tulips, daffodils, crocuses, crysanthemums, and roses when applied to said plants and/or to the soil containing the seeds or other propagating organs of said plants in amounts of as low as from about 0.0001 kg/ha to 0.01 kg/ha and preferably 0.0002 kg/ha to 0.005 kg/ha.

The compounds of formula (I), (Ia), and (II) are disclosed and claimed as herbicides in co-pending application Ser. No. 382,041, filed May 25, 1982, which is a continuation-in-part of application Ser. No. 155,909, filed June 2, 1980.

Advantageously, the compounds of this invention can be formulated as solid or liquid compositions which may be dispersed in a liquid or solid diluent for application to vegetative matter.

Since the formula (I) derivatives, wherein $R_3$ is a salt forming cation, are water soluble, these compounds can simply be dispersed in water and applied as a dilute aqueous spray to the foliage of agronomic and horticultural plants or to soil containing the seeds or other propagating organs thereof. These salts also lend themselves to formulation as flowable concentrates.

The 2-($\alpha$-imidazolin-2-yl)pyridines and quinolines of formula (I) can be formulated as wettable powders, flowable concentrates, emusifiable concentrates, and granular formulations.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 25% by weight of the active ingredient in about 65% by weight of N-methylpyrrolidone, isophorone, butyl cellosolve, methylacetate or the like and dispersing therein about 10% by weight of a nonionic surfactant such as alkylphenoxypolyethoxy alcohol. This concentrate is dispersed in water for application as a liquid spray.

When the above compounds are to be used where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

Wettable powders can be prepared by grinding together about 20% to 45% by weight of a finely divided carrier such as kaolin, bentonite, diatomaceous earth, attapulgite, or the like, 45% to 80% by weight of the active compound, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methyl-pyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

When the compounds of the invention are to be used where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

A composition for the treatment of a one hectare plot, to increase the crop yield of cereal grains or legumes grown thereon, comprises from 100 to 500 liters of water; from 0.01 to 0.001 kg of a compound having the structure:

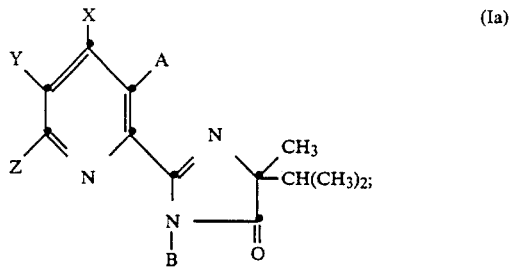

(Ia)

wherein B is hydrogen, CO-alkyl $C_1$-$C_6$ or CO-phenyl; A is $COOR_3$ where $R_3$ is as described in formula (I) above; X is hydrogen and Y and Z each represent hydrogen, $C_1$-$C_6$ alkyl, $C_1$-$C_4$-alkoxy, halo, $C_1$-$C_4$-haloalkyl, or phenyl and, when taken together, YZ represent —$(CH_2)_4$—, and, from 0.01% to 3% by weight of a dispersing agent and/or non-ionic surfactant.

In order to facilitate a further understanding of the invention, the following examples are presented primarily for the purpose of illustrating certain more specific details thereof. The invention is not be be deemed limited thereby except as defined in the claims. Unless otherwise noted, all parts are by weight.

EXAMPLE 1

Evaluation of the maturation effect on Barley caused by the compounds of the invention In the following tests, the appropriate compounds are dissolved or dispersed in acetone-water (1:1) mixtures at the final concentration corresponding to the kg/ha rates indicated in the tables below The solutions also contain 0.1% to 0.25% v/v colloidal BIOFILM ® (a product of Colloidal Products Corp.) which is a mixture of alkyl aryl polyethoxyethanol, free and combined fatty acids, glycol ethers, dialkylbenzene carboxylate and 2propanol.

The plant species used in these tests is barley (Hordeum vulgare, var. Mexico).

The solution or dispersion of the compound under test is sprayed at a rate of 40 ml per pot applied to the foliage.

In the postemergence tests, the plants are seedlings at the two leaf stage (19 plants per pot; pot size; 8.9 cm×6.3 cm×6.3 cm)

The pots were watered immediately before treatment and placed on benches in a random arrangement in the greenhouse. Normal watering and fertilizing practices are followed (pesticides are applied to the plants as needed). Minimum day and night temperatures of 18.3° C. are maintained during cooler periods of the year. Normal daily fluctuations occur during the summer season.

Plants are sprayed to provide the kg/ha rates indicated in the tables below Each treatment is replicated 6 times.

Data Recording

Periodic observations are made after treatment and morphological changes are noted. From these observations as compared to the untreated controls, the maturation effect of the instant compounds on barley can be determined.

The data thus obtained are averaged and summarized in Tables Ia to Ic inclusive.

TABLE Ia

Evaluation of the maturation effect of the compounds of the invention on barley

| Compound | Rate kg/ha | Results |
| --- | --- | --- |
| Triethylammonium-2-(5-isopropyl-5-methyl-4-oxo-2-imidazolin-2-yl)-nicotinate | 0.01 | slight increase in tillering |
|  | 0.002 | slight increase in tillering |
| Methyl-2-(5-isopropyl-5-methyl-4-oxo-2-imidazolin-2-yl)nicotinate | 0.01 | great increase in tillering |
|  | 0.002 | Earlier heading increased tillering |
|  | 0.004 | Earlier heading increased tillering |
| Calcium-2-(5-isopropyl-5-methyl-4-oxo-2-imidazolin-2-yl)nicotinate | 0.01 | Phytotoxic |
|  | 0.002 | Increased tillering |
| 2-(5-ethyl-5-methyl-4-oxo-2-imidazolin-2-yl)-nicotinic acid | 0.01 | delayed heading increased tillering |

TABLE Ib

Evaluation of the maturation effect of the compounds of the invention on barley

| Compound | Rate kg/ha | Results |
| --- | --- | --- |
| Methyl-2-(5-isopropyl-5-methyl-4-oxo-2-imidazolin-2-yl)nicotinate | 0.01 | slight increase in tillering |
|  | 0.005 | slight increase in tillering |

TABLE Ic

Evaluation of the maturation effect of the compounds of the invention on barley

| Compound | Rate kg/ha | Results |
| --- | --- | --- |
| Methyl-2-(5-isopropyl-5-methyl-4-oxo-2-imidazolin-2-yl)nicotinate | 0.1 | Phytotoxic |
|  | 0.05 | Phytotoxic |
|  | 0.01 | great increase in tillering with earlier head maturation |

EXAMPLE 2

Evaluation of the increased branching and flowering effect of the compounds or in the invention By the method of Example 1, the effect of the compounds of the invention is evaluated on soybeans (*Glycine max*, var. ADELPHI). Each test is replicated six times. There is one plant per pot and the plants are treated at the 2nd to 3rd trifoliate stage.

The data obtained are averaged and summarized in Tables IIa to IIc inclusive.

TABLE IIa

Evaluation of the increased branching effect on soybeans of the compounds of the invention

| Compound | Rate kg/ha | Results |
|---|---|---|
| Methyl-2-(5-isopropyl-5-methyl-4-oxo-2-imidazolin-2-yl)nicotinate | 0.01 | greatly increased branching, blossoming delayed, greener leaves |
|  | 0.002 | Increased branching |
| Calcium-2-(5-isopropyl-5-methyl-4-oxo-2-imidazolin-2-yl)nicotinate | 0.01 | greatly increased branching, delayed blossoming, greener leaves |
| 2-(5-ethyl-5-methyl-4-oxo-2-imidazolin 2-yl)nicotinic acid | 0.01 | Moderately increased branching |
|  | 0.0004 | Moderately increased branching |

TABLE IIb

Evaluation of increased branching and flowering effect on soybeans of the compounds of the invention

| Compound | Rate kg/ha | Results |
|---|---|---|
| Methyl-2-(5-isopropyl-5-methyl-4-oxo-2-imidazolin-2-yl)nicotinate | 0.01 | greatly increased branching; increased number of flowers, flowering delayed slightly |
|  | 0.005 | greatly increased branching; moderately increased flowering |
|  | 0.0025 | moderately increased branching; increased flowering |

TABLE IIc

Evaluation of increased tillering effect on soybeans of the compounds of the invention

| Compound | Rate kg/ha | Results |
|---|---|---|
| Methyl-2-(5-isopropyl 5-methyl-4-oxo-2-imidazolin-2-yl)nicotinate | 0.1 | Phytotoxic |
|  | 0.05 | Phytotoxic |
|  | 0.01 | greatly increased branching darker green leaves |

EXAMPLE 3

Evaluation of the increased yield effect of the compounds of the invention

By the method of Example 1, the effect of the compounds of the invention is evaluated on soybeans (Glycine max. var. ADELPHI). Each test is replicated 6 times. There is one plant per pot and the plants are treated at the 6th trifoliate stage. The data obtained are averaged and summarized in Table III below.

TABLE III

Evaluation of the increased yield effect of the compounds of the invention on soybeans (Average of 6 replicates)

| Compound | Rate kg/ha | No. of pods | % Increase (+) Decrease (−) | Fresh pod wt in g | % Increase (+) Decrease (−) | Dry pod wt in g | % Increase (+) Decrease (−) |
|---|---|---|---|---|---|---|---|
| Control | — | 99.7 | — | 126.2 | — | 32.4 | — |
| Methyl-2-(5-isopropyl-5-methyl-4-oxo-2-imidazolin-2-yl)nicotinate | 0.01 | 27.3 | −73 | 28.5 | −77 | 7.7 | −76 |
|  | 0.002 | 115.0 | +15 | 126.3 | 0 | 29.5 | −9 |
|  | 0.0004 | 122.8 | +23 | 149.6 | +19 | 38.2 | +18 |

EXAMPLE 4

Evaluation of the maturation effect on wheat caused by the compounds of the invention applied postemergence By the method of Example 1, wheat (*Triticum aestivum*, var. Era) is treated at the early tillering stage at the kg/ha rates indicated in Table IV below. Each treatment is replicated 6 times.

Data recording

The plants are harvested five weeks post treatment, the number of heads, fresh and dry head weight and straw weight are determined and the % changes (±) indicated. The data obtained are averaged and summarized in Table IV below.

TABLE IV

Evaluation of the maturation effect on wheat, caused by the compounds of the invention, applied postemergence

| Compound | Rate kg/ha | Heads; No.; wt in g; % change | | | Straw; wt in g; % change |
|---|---|---|---|---|---|
| | | No. of heads; % change | Fresh wt in g; % change | Dry wt in g; % change | |
| Control | — | 30.2 | 64.3 | 30.1 | 100.1 |
| | | — | — | — | — |
| ethyl-2-(5-isopropyl-4-oxo-imidazolin-2-yl)-nicotinate | 0.01 | 37.0 | 77.3 | 30.8 | 173.5 |
| | | 22.5 | 20.2 | 2.3 | 73.3 |
| | 0.002 | 38.2 | 88.0 | 38.4 | 160.7 |
| | | 26.5 | 36.8 | 27.6 | 60.5 |
| | 0.004 | 31.5 | 62.2 | 28.2 | 110.8 |
| | | 4.3 | −3.1 | −6.3 | 10.7 |

EXAMPLE 5

Evaluation of the maturation effect on wheat caused by the compounds of the invention applied preemergence The seeds of wheat (*Triticum aestivum,* var. Era) are mixed with potting soil and planted on top of approximately 2.5 cm of soil in 12.5 cm diameter fiber pots. After planting, the pots are sprayed with the aqueous acetone solution containing the test compound at the kg/ha rates given in Table V below. The treated cups are then placed on greenhouse benches, watered and cared for in accordance with conventional greenhouse procedures. Each treatment is replicated six times.

Data recording

The plants are harvested 11 weeks post treatment, the number of heads, fresh and dry head weight and straw weight are determined and the % changes (±) indicated. The data obtained are averaged and summarized in Table V below.

TABLE V

Evaluation of the maturation effect on wheat, caused by the compounds of the invention, applied preemergence

| Compound | Rate kg/ha | No. of heads; % change | Fresh wt in g; % change | Dry wt in g; % change | Straw wt in g; % change |
| --- | --- | --- | --- | --- | --- |
| Control | — | 25.7 — | 47.2 — | 15.7 — | 145.3 — |
| Methyl-2-(5-isopropyl-5-methyl-4-oxo-2-imidazolin-2-yl)-nicotinate | 0.1 | — | — | — | 101.6 −30.1 |
|  | 0.01 | 29.3 14.0 | 50.9 7.8 | 17.0 8.3 | 139.8 −3.8 |
|  | 0.001 | 28.8 12.1 | 53.0 12.3 | 18.0 14.6 | 135.3 −6.9 |

EXAMPLE 6

Evaluation of test compounds for increasing soybean yield

In the following tests, seeds of either Era variety wheat or Adelphi variety soybeans, are planted in 13 cm fiber pots. The test compounds are then dispersed in acetone-water (1:1) mixtures containing 0.1% to 0.25% v/v colloidal BIOFILM which is a mixture of alkyl aryl polyethoxyethanol, free and combined fatty acids, glycol ethers, dialkylbenzene carboxylate and 2-propanol. The planted seeds are sprayed with a sufficient amount of the mixture to provide each pot with 0.1, 0.01, or 0.001 kg/ha of test compound. The treated cups are then placed on greenhouse benches and cared for in accordance with greenhouse procedures. Three months after treatment the soybeans are harvested, dried and weighed. Six replicates per treatment are used and averaged. Data obtained are reported below.

TABLE VI

Soybean yield enhancement evaluation

| Compound | Rate kg/ha | Dry Pod wt (g) | % Increase over controls |
| --- | --- | --- | --- |
| Untreated controls | — | 13 | — |
| Methyl 2-(5-isopropyl-5-methyl-4-oxo-2-imidazolin-2-yl)-nicotinate | 0.1 | 4.8 |  |
|  | 0.01 | 14.9 | +15 |
|  | 0.001 | 15.3 | +18 |

Wheat yield enhancement evaluation

| Compound | Rate kg/ha | Dry Head wt (g) | % Increase over controls |
| --- | --- | --- | --- |
| Untreated controls | — | 15.7 | — |

TABLE VI-continued

| | | | |
| --- | --- | --- | --- |
| Methyl 2-(5-isopropyl-5-methyl-4-oxo-2-imidazolin-2-yl)-nicotinate | 0.1 | — | |
| | 0.01 | 17.0 | +8.2 |
| | 0.001 | 18.0 | +14.6 |
| Untreated control | — | 19.3 | — |
| methyl 2-(5-isopropyl-5-methyl-4-oxo-2-imidazolin-2-yl)-nicotinate)·HCl | 0.016 | 11.3 | |
| | 0.008 | 21.5 | +11.4 |
| | 0.004 | 23.2 | +14.5 |

EXAMPLE 7

Wheat yield enhancement evaluation, test compound applied post-emergence

The following tests were conducted using the procedure of Example 1, excepting that the plant species used is Era wheat and the crop is harvested nine weeks after treatment, the following results are obtained.

Wheat Yield Enhancement Evaluation

| Compound | Rate kg/ha | Dry Head wt (g) | % Increase over controls |
| --- | --- | --- | --- |
| Untreated controls | — | 30.1 | — |
| Methyl 2-(5-isopropyl-5-methyl-4-oxo-2-yl)nicotinate | 0.01 | 30.8 | +2.3 |
| | 0.002 | 38.4 | +28.1 |
| | 0.0004 | 28.2 | −6.3 |

EXAMPLE 8

Evaluation of test compounds for crop yield enhancement employing soybeans (*Glycine max.* variety Adelphi) as the crop plant In the following tests, the appropriate compounds are dissolved or dispersed in acetone-water (1:1) mixtures at the final concentration corresponding to the kg/ha rates indicated in Table Vll below. The solutions also contain 0.1% to 0.25% v/v colloidal BIOFILM ® (a product of Colloidal Products Corporation) which is a mixture of alkyl aryl polyethoxyethanol, free and combined fatty acids, glycol ethers, dialkylbenzene carboxylate and 2propanol.

The plant species used in these tests is soybeans (*Glycine max.* variety Adelphi).

The plants are at the fifth to sixth trifoliate stage when treated and are growing in individual pots, pot size: 8.9 cm × 6.3 cm × 6.3 cm.

The pots are watered immediately before treatment and placed on benches in a random arrangement in the greenhouse. Normal watering and fertilizing practices are followed (pesticides are applied to the plants as needed). Minimum day and night temperatures of 18.3°

C. are maintained during cooler periods of the year. Normal daily fluctuations occur during the summer season.

The solution or dispersion of the compound under test is sprayed in a volume of 40 mL applied to the foliage of four to six replicates at a rate corresponding to the indicated kg/ha rate reported in Table VII below.

Forty-five days after treatment, the beans from each plant are harvested and weighed. Data obtained are reported in Table VII below.

TABLE VII

EVALUATION OF TEST COMPOUNDS FOR CROP YIELD ENHANCEMENT EMPLOYING SOYBEANS (GLYCINE MAX. VARIETY ADELPHI) AS THE CROP PLANT

| Compound | Rate kg/ha | Average Bean Dry Weight (g) | Percent of Control |
|---|---|---|---|
| Control | — | 15.7 | — |
| 2-(5-Isopropyl-5-methyl-4-oxo-2-imidazolin-2-yl)-3-quinolinecarboxylic acid | 0.005 | 17.7 | 112.7 |
|  | 0.0025 | 16.9 | 107.6 |
|  | 0.0005 | 17.0 | 108.2 |
| Control | — | 9.0 | — |
| Cyclohexyl 2-(5-Isopropyl-5-methyl-4-oxo-2-imidazolin-2-yl)nicotinate | 0.063 | 9.4 | 104.4 |
|  | 0.036 | 10.1 | 112.2 |
| Methyl 5-ethyl-2-(5-isopropyl-5-methyl-4-oxo-2-imidazolin-2-yl)-nicotinate | 0.063 | 9.5 | 105.5 |
|  | 0.036 | 9.8 | 108.8 |
| Control | — | 13.2 | — |
| 2-(4-oxo-1,3-diazaspiro[4.5]dec-2-en-2-yl)nicotinic acid | 0.063 | 14.0 | 107.7 |
|  | 0.036 | 13.0 | 98.5 |
|  | 0.015 | 14.9 | 112.9 |
| Calcium 2-(4-oxo-1,3-diazaspiro[4.5]dec-2-en-2-yl)nicotinate | 0.015 | 13.9 | 105.4 |
| Tallowammonium 2-(4-oxo-1,3-diazaspiro[4.5]dec-2-en-2-yl)nicotinate | 0.15 | 15.3 | 115.9 |
| 2,2'-Iminodiethanol 2-(4-oxo-1,3-diazaspiro[4.5]dec-2-en-2-yl)-nicotinate | 0.036 | 14.2 | 107.6 |
|  | 0.015 | 14.4 | 109.1 |
| Control | — | 21.0 | — |
| 6-Chloro-2-(5-isopropyl-5-methyl-4-oxo-2-imidazolin-2-yl)-3-quinolinecarboxylic acid | 0.250 | 21.4 | 101.9 |
|  | 0.125 | 22.3 | 106.2 |
|  | 0.063 | 22.1 | 105.2 |
| 5-Chloro-2-(5-isopropyl-5-methyl-4-oxo-2-imidazolin-2-yl)-3-quinolinecarboxylic acid | 0.250 | 20.9 | 99.5 |
|  | 0.125 | 25.2 | 120.0 |
|  | 0.063 | 21.2 | 101.0 |
| 2-(5-Isopropyl-5-methyl-4-oxo-2-imidazolin-2-yl)-6-nitro-3-quinolinecarboxylic acid | 0.063 | 26.2 | 124.8 |
| Methyl 5-ethyl-2-(5-isopropyl-5-methyl-4-oxo-2-imidazolin-2-yl)nicotinate | 0.0250 | 25.0 | 119.0 |
|  | 0.125 | 22.5 | 107.1 |
|  | 0.063 | 23.1 | 110.0 |
| Control | — | 27.8 | — |
| Magnesium 2-(4-oxo-1,3-diazaspiro[4.5]dec-2-en-2-yl)nicotinate | 0.25 | 29.2 | 105.0 |
| Ferrous 2-(4-oxo-1,3-diazaspiro[4.5]dec-2-en-2-yl)nicotinate | 0.50 | 30.3 | 108.9 |
| Sodium 2-(4-oxo-1,3-diazaspiro[4.5]dec-2-en-2-yl)nicotinate | 0.25 | 28.7 | 103.2 |

EXAMPLE 9

Evaluation of test compounds for increasing crop yield of wheat (*Triticum aestivum*, variety Era)

The seeds of wheat (*Triticum aestivum*, variety Era) are mixed with potting soil and planted on top of approximately 2.5 cm of soil in 12.5 cm diameter fiber pots. After planting, the pots are sprayed with the aqueous acetone solution containing the test compound at the kg/ha rates given in Table VIII below. The treated cups are then placed on greenhouse benches, watered, and cared for in accordance with conventional greenhouse procedures. Each treatment is replicated six times.

Data Recording

The plants are harvested 11 weeks post treatment, the dry head weight determined, and the percent changes (+) dry head weight of the untreated controls indicated. Data obtained are averaged and summarized in Table VIII below.

TABLE VIII

EVALUATION OF TEST COMPOUNDS FOR INCREASING CROP YIELD OF WHEAT (VARIETY ERA)

| Compound | Rate kg/ha | Wheat Yield Dry Head Weight (g) Per Pot | Percent of Control |
|---|---|---|---|
| Control | — | 16.4 | — |
| 2-(5,5-dimethyl-4-oxo-2-imidazolin-2-yl)nicotinic acid | 0.125 | 26.4 | 161.0 |
|  | 0.063 | 19.0 | 115.8 |
|  | 0.036 | 23.3 | 142.0 |
| Cyclohexyl 2-(5-isopropyl-5-methyl-4-oxo-2-imidazolin-2-yl)nicotinate | 0.063 | 18.3 | 111.6 |
| Methyl 2-(5-isopropyl-5-methyl-4-oxo-2-imidazolin-2-yl)-6-methoxynicotinate | 0.063 | 30.4 | 185.4 |
|  | 0.036 | 16.8 | 102.4 |
| Control | — | 23.2 | — |
| 2-Propynyl 2-(5,5-dimethyl-4-oxo-2-imidazolin-2-yl)-nicotinate | 0.125 | 23.5 | 101.3 |
| Methyl 2-(5-ethyl-5-methyl-4-oxo-2-imidazolin-2-yl)-nicotinate | 0.036 | 26.7 | 115.1 |
| Methyl 2-(5-isobutyl-5-methyl-4-oxo-2-imidazolin-2-yl)nicotinate | 2.0 | 25.5 | 110.0 |
|  | 1.0 | 27.6 | 118.9 |

EXAMPLE 10

Evaluation of test compounds for crop yield enhancement employing soybeans (*Glycine max.* variety Adelphi) as the crop plant In the following tests, the appropriate compounds are dissolved or dispersed in acetone-water (1:1) mixtures at the final concentration corresponding to the kg/ha rates indicated in Table IX below. The solutions also contain 0.1% to 0.25% v/v colloidal BIOFILM ® (a product of Colloidal Products Corporation) which is a mixture of alkyl aryl polyethoxyethanol, free and combined fatty acids, glycol ethers, dialkylbenzene carboxylate and 2-propanol.

The plant species used in these tests is soybeans (*Glycine max.* variety Adelphi).

The plants are at the fifth to sixth trifoliate stage when treated and are growing in individual pots, pot size: 8.9 cm × 6.3 cm × 6.3 cm.

The pots are watered immediately before treatment and placed on benches in a random arrangement in the greenhouse. Normal watering and fertilizing practices are followed (pesticides are applied to the plant as needed). Minimum day and night temperatures of 18.3° C. are maintained during cooler periods of the year. Normal daily fluctuations occur during the summer season.

The solution or dispersion of the compound under test is sprayed in a volume of 40 mL applied to the foliage of six replicates at a rate corresponding to the indicated kg/ha rate reported in Table IX below.

Forty-five days after treatment, the beans from each plant are harvested and weighed. Data obtained are reported in Table IX below.

TABLE IX

Evaluation of Test Compounds for Crop Yield Enhancement Employing Soybeans (Glycine max. variety Adelphi) as the Crop Plant

| Compound | Rate kg/ha | Percent ± Control |
|---|---|---|
| Methyl 2-(5-isopropyl-5-methyl-4-oxo-2-imidazolin-2-yl)-nicotinate | 0.0025 | −9.9 |
| | 0.00125 | +2.5 |
| | 0.00062 | +12.6 |
| 2-(5-Isopropyl-5-methyl-4-oxo-2-imidazolin-2-yl)nicotinic acid | 0.0025 | +8.6 |
| | 0.00125 | +20.0 |
| | 0.00062 | +2.3 |
| *2-Methylallylammonium 2-(5-isopropyl-5-methyl-4-oxo-2-imidazolin-2-yl)nicotinate | 0.0025 | +21.4 |
| | 0.00125 | +25.2 |
| | 0.00062 | −8.0 |
| *5-Ethyl-2-(5-isopropyl-5-methyl-4-oxo-2-imidazolin-2-yl)nicotinic acid | 0.0025 | +9.2 |
| | 0.00125 | +9.5 |
| | 0.00062 | +29.6 |

*Applied at seventh-eighth trifoliate

EXAMPLE 11

Evaluation of test compounds for increasing crop yield of winter barley (variety Maury)

In the following tests, 18 m² plots were seeded with winter barley (variety Maury). When the barley was established and had developed to the Zadok's 30/31 stage, i.e., late tillering, the plots were sprayed with a dilute aqueous solution containing 0.25% by weight of Ortho-X77 spreader activator, the principal ingredients of which are: alkylarylpolyoxyethylene glycol, free fatty acid and propanol, and a sufficient amount of test compound to provide 0.125 g/ha, 0.25 g/ha or 0.5 g/ha of active ingredient when the solution is applied at the rate of 790 liters per hectare. The barley is permitted to mature and then harvested. Crop yield data obtained in these tests are reported in Table X below.

TABLE X

Evaluation of Test Compounds for Increasing Crop Yield of Winter Barley (variety Maury)

| Compound | Rate kg/ha | Plot Yield kg/18 m² Plot | Percent Control |
|---|---|---|---|
| Control | 0 | 9.65 | — |
| Isopropylammonium 2-(5-iospropyl-5-methyl-4-oxo-2-imidazolin-2-yl)nicotinate | 0.000125 | 9.85 | 102.1 |
| | 0.00025 | 9.99 | 103.5 |
| | 0.0005 | 9.82 | 101.8 |
| Control | 0 | 9.05 | — |
| 5-Ethyl-2-(5-isopropyl-5-methyl-4-oxo-2-imidazolin-2-yl)nicotinic acid | 0.000125 | 9.28 | 102.5 |
| | 0.00025 | 9.08 | 100.3 |
| | 0.0005 | 9.19 | 101.5 |

EXAMPLE 12

Evaluation of the maturation effect on barley caused by the compounds of the invention In the following tests, the appropriate compounds are dissolved or dispersed in acetone-water (1:1) mixtures at the final concentration corresponding to the kg/ha rates indicated in the tables below. The solutions also contain 0.1% to 0.25% v/v collodal BIOFILM ® (a product of Colloidal Products Corp.) which is a mixture of alkyl aryl polyethoxyethanol, free and combined fatty acids, glycol ethers, dialkylbenzene carboxylate and 2-propanol.

The plant species used in these tests is barley (*Hordeum vulgare*, var. Mexico).

The solution or dispersion of the compound under test is sprayed at a rate of 40 mL per pot applied to the foliage.

In the postemergence tests, the plants are seedlings at the two leaf stage (19 plants per pot; pot size; 8.9 cm × 6.3 cm × 6.3 cm).

The pots were watered immediately before treatment and placed on benches in a random arrangement in the greenhouse. Normal watering and fertilizing practices are followed (pesticides are applied to the plants as needed). Minimum day and night temperatures of 18.3° C. are maintained during cooler periods of the year. Normal daily fluctuations occur during the summer season.

Plants are sprayed to provide the kg/ha rates indicated in the tables below. Each treatment is replicated six times.

Data Recording

Periodic observations are made after treatment and morphological changes are noted. From these observations as compared to the untreated controls, the maturation effect of the instant compounds on barley can be determined.

The data thus obtained are summarized in Table XI below.

TABLE XI

Evaluation of the maturation effect of the compounds of the invention on barley

| Compound | Rate kg/ha | Results |
|---|---|---|
| 3-Methyl-3-butenyl 2-(5-isopropyl-5-methyl-4-oxo-2-imidazolin-2-yl) 3-quinolinecarboxylic acid | 0.10 | Earlier heading Increased number of blooms |
| 6-Chloro-2-(5-isopropyl-5-methyl-4-oxo-2-imidazolin-2-yl) 3-quinolinecarboxylic acid | 0.1 | Earlier heading |
| | 0.05 | Earlier heading |
| 2-(5-Isopropyl-5-methyl-4-oxo-2-imidazolin-2-yl)-7-methyl-3-quinolinecarboxylic acid | 0.1 | Earlier heading |
| | 0.05 | Earlier heading |
| 6-Fluoro-2-(5-isopropyl-5-methyl-4-oxo-2-imidazolin-2-yl) 3-quinolinecarboxylic acid | 0.025 | Earlier heading |
| 6-Butoxy-2-(5-isopropyl-5-methyl-4-oxo-2-imidazolin-2-yl) 3-quinolinecarboxylic acid | 0.5 | Earlier heading Increased number of blooms |
| | 0.25 | Earlier heading Increased number of blooms |
| tert-Butyl 2-(4-isopropyl-5-methyl-4-oxo-2-imidazolin-2-yl) 3-quinolinecarboxylic acid | 0.20 | Earlier heading |
| Methyl 2-(5-isopropyl-5-methyl-4-oxo-2-imidazolin-2-yl)-5-propylnicotinate | 0.25 | Earlier heading Increased number of blooms |
| 2-(5-Isopropyl-5-methyl-4-thioxo-2-imidazolin-2-yl) 3-quinolinecarboxylic acid | 0.01 | Earlier heading |
| Methyl 1-oxide 2-(1-acetyl-5-isopropyl-5-methyl-4-oxo-2-imidazolin-2-yl) 3-quinolinecarboxylate | 0.50 | Earlier heading |
| 2-(5-Ethyl-5-methyl-4-oxo-2-imidazolin-2-yl) 3-quinolinecarboxylic acid | 0.10 | Earlier heading Increased number of blooms |
| 5-Chloro-2-(5-isopropyl-5-methyl-4-oxo-2-imidazolin-2-yl)-8-methoxy-3-quinolinecarboxylic acid | 0.05 | Earlier heading |
| | 0.025 | Earlier heading |
| 8-Chloro-2-(5-isopropyl-5-methyl-4-oxo-2-imidazolin-2-yl)-5-methoxy-3-quinolinecarboxylic acid | 0.25 | Earlier heading Increased number of blooms |

TABLE XI-continued
Evaluation of the maturation effect of the compounds of the invention on barley

| Compound | Rate kg/ha | Results |
|---|---|---|
| 2-Propynyl 5-ethyl-2-(5-isopropyl-5-methyl-4-oxo-2-imidazolin-2-yl) nicotinate | 0.10 | Earlier heading Increased number of blooms |
| Ethyl 5-ethyl-2-(5-isopropyl-5-methyl-4-oxo-2-imidazolin-2-yl) nicotinate | 0.25 | Earlier heading Increased number of blooms |
| | 0.125 | Earlier heading Increased number of blooms |
| 2-(5-Isopropyl-5-methyl-4-oxo-2-imidazolin-2-yl)-6-(trifluoromethyl)-3-quinolinecarboxylic acid | 0.05 | Earlier heading Increased number of blooms |
| 6-(Allyloxy)-2-(5-isopropyl-5-methyl-4-oxo-2-imidazolin-2-yl)nicotinic acid | 0.025 | Earlier heading |
| Methyl 2-(5-isopropyl-5-methyl-4-oxo-2-imidazolin-2-yl) 3-quinolinecarboxylate | 0.10 | Earlier heading Increased number of blooms |
| 7-Chloro-2-(5-isopropyl-5-methyl-4-oxo-2-imidazolin-2-yl) 3-quinolinecarboxylic acid | 0.10 | Earlier heading Increased number of blooms |
| 2-(5-Isopropyl-5-methyl-4-oxo-2-imidazolin-2-yl)-5-methoxynicotinic acid, compound with isopropylamine (1:1) | 0.005 | Earlier heading Increased number of blooms |
| Benzyl 2-(5-isopropyl-5-methyl-4-oxo-2-imidazolin-2-yl)-5-methylnicotinate | 0.025 | Earlier heading |
| 2-Propynyl 2-(5-isopropyl-5-methyl-4-oxo-2-imidazolin-2-yl) 3-quinolinecarboxylate | 0.025 | Earlier heading |
| 1,1-Dimethylallyl 2-(5-isopropyl-5-methyl-4-oxo-2-imidazolin-2-yl) 3-quinolinecarboxylate | 0.005 | Earlier heading |
| 2-Propynyl 2-(1-acetyl-5-isopropyl-5-methyl-4-oxo-2-imidazolin-2-yl)nicotinate | 0.025 | Earlier heading Increased number of blooms |
| 2-(5-Isopropyl-5-methyl-4-oxo-2-imidazolin-2-yl)-5-methylnicotinic acid | 0.025 | Earlier heading Increased number of blooms |
| Benzyl 5-isopropoxy-2-(5-isopropyl-5-methyl-4-oxo 2-imidazolin-2-yl)nicotinate | 0.025 | Earlier heading Increased number of blooms |
| Methyl 6-butyl-5-ethyl-2-(5-isopropyl-5-methyl-4-oxo-2-imidazolin-2-yl)nicotinate | 0.5 0.25 | Earlier heading Earlier heading |
| 2-(5-Isopropyl-5-methyl-4-oxo-2-imidazolin-2-yl)-6-(2-propynyloxy) nicotinic acid | 0.10 | Earlier heading Increased number of blooms |
| | 0.01 | Earlier heading Increased number of blooms |
| Benzyl 5-ethyl-2-(5-isopropyl-5-methyl-4-oxo-2-imidazolin-2-yl)nicotinate | 0.125 | Earlier heading Increased number of blooms |
| 2-(5-Isopropyl-5-methyl-4-oxo-2-imidazolin-2-yl)-5,8-dimethoxy-3-quinolinecarboxylic acid | 0.01 | Earlier heading Increased number of blooms |
| 2-(5-Isopropyl-5-methyl-4-oxo-2-imidazolin-2-yl)-6,7-dimethyl-3-quinolinecarboxylic acid | 0.20 0.05 | Earlier heading Increased number of blooms Earlier heading Increased number of blooms |

EXAMPLE 13

Evaluation of test compounds for increasing soybean blooms

In the following tests, seeds of Adelphi variety soybeans are planted in 13 cm fiber pots. The test compounds are then dispersed in acetone-water (1:1) mixtures containing 0.1% to 0.25% v/v colloidal BIOFILM ® which is a mixture of alkyl aryl polyethoxyethanol, free and combined fatty acids, glycol ethers, dialkylbenzene carboxylate and 2-propanol. The planted seeds are sprayed with a sufficient amount of the mixture to provide each pot with 0.2, 0.125 and 0.10 kg/ha of test compound. The treated cups are then placed on greenhouse benches and cared for in accordance with greenhouse procedures. Three to four weeks after treatment the number of blooms are counted and compared to an untreated control. Data obtained are reported below in Table XII.

TABLE XII
Evaluation of test compounds for bloom enhancement employing soybeans (Glycine max. variety Adelphi) as the crop plant

| Compound | Rate kg/ha | Bloom Percent ± Control |
|---|---|---|
| 2-(5-Isopropyl-5-methyl-4-oxo-2-imidazolin-2-yl) benzo[g]quinoline-3-carboxylic acid | 0.20 | +10 |
| 6-Ethoxy-2-(5-isopropyl-5-methyl-4-oxo-2-imidazolin-2-yl) 3-quinolinecarboxylic acid | 0.10 | +10 |

EXAMPLE 14

Evaluation of compounds for increasing yields in soybeans

In the following tests, seeds of soybeans (598 on J-99 variety) are planted in 15.24 cm × 12.7 cm pots. Some seeds are then treated preemergence while others are allowed to grow to the two to three trifoliate ($V_3$) stage or five to six trifoliate ($V_5$) stage. The plants or seeded pots are sprayed with various concentrations of chemicals being evaluated in acetone/water solutions containing 0.25% v/v of colloidal BIOFILM ® which is a mixture of alkyl aryl polyethoxyethanol, free and combined fatty acids, glycol ethers, dialkylbenzene carboxylate and 2-propanol. The treated plants and pots are then returned to the greenhouse and cared for in accordance with greenhouse procedures. The plants are allowed to mature to the $R_8$ stage and are harvested, and the yields compared to an untreated control. The results of these experiments, which are summarized in Table XIII, demonstrate the effectiveness of the compounds of the invention for increasing the yield of soybeans as expressed in the number of developed fruit, dry weight and fresh weight.

TABLE XIII
EVALUATION OF TEST COMPOUNDS FOR INCREASING YIELDS OF SOYBEANS

| Compound | Stage of Application | Day | Rate kg/ha | Percent Yield Compared With Untreated Control | | |
|---|---|---|---|---|---|---|
| | | | | Number Fruit Development | Yield Dry Weight | Yield Fresh Weight |
| 2-(4-Isopropyl-4-methyl-5-oxo-2-imidazolin-2-yl)-6-p-tolyl-nicotinic acid | $V_3$ | 75 | 63 | 110.33 | 114.65 | 125.91 |
| | $V_3$ | 75 | 32 | 108.06 | 109.11 | 116.21 |
| | $V_3$ | 75 | 16 | 99.24 | 107.74 | 104.75 |
| Ethyl 6-ethyl-2-(4-isopropyl-4-methyl-5-oxo-2-imidazolin-2-yl)-Nicotinate | PE | 97 | 1000 | 97.31 | 102.99 | 101.58 |
| | PE | 97 | 500 | 98.92 | 97.23 | 118.31 |
| | PE | 97 | 250 | 104.84 | 104.29 | 104.14 |
| 5-Hydroxy-2-(4-iospropyl-4-methyl-5-oxo-2-imidazolin-2-ly)-nicotinic acid | PE | 96 | 5.0 | 100.00 | 97.85 | 96.89 |
| | PE | 96 | 2.5 | 91.65 | 93.60 | 99.46 |
| | PE | 96 | 1.3 | 95.23 | 103.70 | 106.22 |
| 1,1-Dimethyl-2-propynl-2-(4-iospropyl-4-methyl-5-oxo-2-imidazolin-2-yl)-nicotinate | $V_3$ | 69 | 5.0 | 106.63 | 106.62 | 102.15 |
| | $V_3$ | 69 | 2.5 | 104.50 | 99.93 | 96.56 |
| | $V_3$ | 69 | 1.3 | 104.42 | 109.15 | 105.71 |
| 2-(4-Isopropyl-4-methyl-5-oxo-2-imidazolin-2-yl)-3-quinolinecarboxylic acid, compound with 2-amino-2,3-dimethylbutyramide (1:1) | $V_3$ | 69 | 125 | 80.76 | 81.07 | 85.94 |
| | $V_3$ | 69 | 63 | 106.31 | 105.00 | 101.75 |
| | $V_3$ | 69 | 32 | 105.68 | 101.34 | 103.46 |
| 2-(4-Iospropyl-4-methyl-5-oxo-2-imidazolin-2-yl)-N-(phenylsulfonyl)-3-quinolinecarboxamide | $V_3$ | 79 | 5.0 | 86.74 | 82.59 | 88.70 |
| | $V_3$ | 79 | 2.5 | 93.18 | 82.70 | 89.23 |
| | $V_3$ | 79 | 1.3 | 104.87 | 104.91 | 102.46 |
| Methyl 6-(dimethylamino)-2-(4-isopropyl-4-methyl-5-oxo-2-imidazolin-2-yl)-3-quinolinecarboxylate | $V_3$ | 83 | 125 | 100.26 | 103.23 | 119.42 |
| | $V_3$ | 83 | 25 | 109.51 | 104.66 | 106.15 |
| | $V_3$ | 83 | 5.0 | 106.68 | 101.18 | 90.48 |
| Ethyl 6-isopropoxy-2-(4-isopropyl-4-methyl-5-oxo-2-imidazolin-2-yl)-nicotinate | $V_3$ | 83 | 100 | 102.83 | 98.88 | 100.93 |
| | $V_3$ | 83 | 50 | 107.20 | 96.02 | 89.30 |
| | $V_3$ | 83 | 25 | 107.71 | 100.31 | 106.45 |
| 7-Ethoxy-2-(4-isopropyl-4-methyl-5-oxo-2-imidazolin-2-yl)-3-quinolinecarboxylic acid | $V_5$ | 79 | 2.5 | 80.59 | 82.81 | 82.80 |
| | $V_5$ | 79 | 1.3 | 100.37 | 109.36 | 107.31 |
| | $V_5$ | 79 | 0.6 | 96.34 | 108.69 | 106.97 |
| 5-Chloro-2-(4-isopropyl-4-methyl-5-oxo-2-imidazolin-2-yl)-3-quinolinecarboxylic acid | $V_5$ | 84 | 50 | 104.00 | 114.35 | 125.09 |
| | $V_5$ | 84 | 25 | 100.80 | 96.68 | 93.41 |
| | $V_5$ | 84 | 13 | 104.40 | 99.25 | 95.60 |

EXAMPLE 15

Evaluation of compounds for increasing yields in cotton

In the following tests, seeds of cotton (Stoneville 213 variety) are planted in 20.32 cm diameter pots and are allowed to grow to the two- to three-leaf ($V_3$) stage or to the first-flower ($R_8$) stage. The plants are sprayed with various concentrations of chemicals being evaluated in acetone/water solutions containing 0.25% v/v of colloidal BIOFILM ® which is a mixture of alkyl aryl polyethoxyethanol, free and combined fatty acids, glycol ethers, dialkylbenzene carboxylate and 2-propanol. The treated plants are then returned to the greenhouse and cared for in accordance with greenhouse procedures. The plants are allowed to mature to the open boll stage and are harvested, and the yields compared to an untreated control. The results of these experiments, which are summarized in Table XIV, demonstrate the effectiveness of some of the compounds of the invention for increasing yields in cotton as expressed in both the dry weight and the number of developed fruits.

TABLE XIV
EVALUATION OF TEST COMPOUNDS FOR INCREASING YIELDS OF COTTON

| Compound | Stage of Application | day | Rate kg/ha | Percent Yield Compared With Untreated Control | |
|---|---|---|---|---|---|
| | | | | Number of Bolls | Developed Bolls Dry Weight |
| 2-(4-Isopropyl-4-methyl-5-oxo-2-imidazolin-2-yl)-6p-tolyl-nicotinic acid | $V_3$ | 113 | 380 | 148.28 | 134.27 |
| | $V_3$ | 113 | 125 | 124.14 | 96.38 |
| | $V_3$ | 113 | 40 | 106.90 | 99.65 |
| 2-(4-Isopropyl-4-methyl-5-oxo-2-imidazolin-2-yl)-3-quinolinecarboxylic acid, compound with 2-amino-2,3-dimethylbutyramide (1:1) | $V_3$ | 113 | 3.0 | 147.13 | 176.69 |
| | $V_3$ | 113 | 2.0 | 106.90 | 104.65 |
| | $V_3$ | 113 | 1.0 | 103.45 | 106.72 |
| 5-Ethyl-2-(4-isopropyl-4-methyl-5-oxo-2-imidazolin-2-yl)-nicotinic acid | $R_8$ | 70 | 6.0 | 69.23 | 68.75 |
| | $R_8$ | 70 | 3.0 | 94.23 | 92.20 |
| | $R_8$ | 70 | 1.5 | 107.69 | 113.33 |

EXAMPLE 16

Evaluation of test compounds for increasing tillering and tonnage of sugarcane as well as sugar yield In this evaluation, sugarcane in the spike stage of growth is sprayed with an aqueous solution of test compound containing a sufficient quantity thereof to provide the desired amount of test compound calculated on a kg/hectare basis. Test solutions contain 0.25% of a nonionic surfactant marketed by GAF Corporation as Igepal DM-710. This surfactant is an alkylphenoxypoly(ethyleneoxy)ethanol. Treatment plots are based on 40 m row/plot, and each treatment is replicated four times. Twenty days after treatment, each plot is examined, and the stand count for each treatment made. Data obtained are reported in Table XV below. One hundred and eleven days after treatment, tiller counts are made, and data obtained are reported in Table XVI below. Eleven months after treatment, the cane is harvested, and the cane yield in metric tons, sugar yield in metric tons, and the number of millable canes from each treatment are determined. Data obtained are reported in Table XVII below.

TABLE XV
DETERMINATION OF STAND COUNT IN SUGARCANE FOLLOWING TREATMENT AT THE SPIKE STAGE

| Compound | Rate (kg/ha) | Stand Count* | Percent Over Control |
|---|---|---|---|
| Untreated Check | 0 | 292 | — |
| Isopropylammonium 2-(4-isopropyl-4-methyl-5-oxo-2-imidazolin-2-yl)nicotinate | 0.1875 | 341 | +16.8 |
|  | 0.375 | 335 | +14.7 |
|  | 0.50 | 321 | +9.9 |

*Based on 40 m row/plot.

TABLE XVI
DETERMINATION OF TILLERING IN SUGARCANE FOLLOWING TREATMENT AT THE SPIKE STAGE

| Compound | Rate (kg/ha) | Average # Tillers | Percent Over Control |
|---|---|---|---|
| Untreated Check | 0 | 622 | — |
| Isopropylammonium 2-(4-isopropyl-4-methyl-5-oxo-2-imidazolin-2-yl)nicotinate | 0.1875 | 689 | +10.0 |
|  | 0.375 | 710 | +14.0 |
|  | 0.50 | 714 | +15.0 |

TABLE XVII
DETERMINATION CANE YIELD, SUGAR YIELD, AND NUMBER OF MILLABLE CANES IN SUGARCANE TREATED AT THE SPIKE STAGE

| Compound | Rate (kg/ha) | Cane Yield M.T./ha* | % Increase Over Weeded Checks | Sugar Yield M.T./ha* | % Increase Over Weeded Checks | Number Millable Canes | % Increase Over Weeded Checks |
|---|---|---|---|---|---|---|---|
| Untreated Check | 0 | 103.6 | — | 11.38 | — | 400 | — |
| Isopropylammonium 2-(4-isopropyl-4-methyl-5-oxo-2-imidazolin-2-yl-nicotinate | 0.1875 | 120.2 | +16.0 | 12.41 | +9.0 | 451 | +12.8 |
|  | 0.375 | 124.5 | +20.2 | 13.97 | +22.8 | 456 | +14.0 |
|  | 0.50 | 120.2 | +16.0 | 13.61 | +12.0 | 450 | +12.5 |

*Metric Tons

EXAMPLE 17

Evaluation of test compounds for the preemergence treatment of seed pieces

In this evaluation, a sufficient amount of isopropylammonium 2-(4-isopropyl-4-methyl-5-oxo-2-imidazolin-2-yl)nicotinate is dissolved in water and sprayed over two-meter long rows of planted sugar cane seed pieces. The plots are permitted to develop and grow for 90 days after treatment and then examined, and the number of stalks per 2 m of row counted. The plots are permitted to grow and then harvested nine months after treatment. Data obtained are reported in Table XVIII below.

TABLE XVIII
EVALUATION OF TEST COMPOUNDS FOR PREEMERGENCE TREATMENT OF SUGARCANE SEED PIECES

| Compound | Rate (g/ha) | # Stalks 2 m of Row 90 DAT* | % Sugar Yield over Control |
|---|---|---|---|
| Untreated Check | 0 | 27 | — |
| Isopropylammonium 2-(4-isopropyl-4-methyl-5-oxo-2-imidazolin-2-yl)-nicotinate | 100 | 44 | +30.5 |
|  | 125 | 38 | +30.5 |

*Days After Treatment

We claim:

1. A method to increase axillary branching, tillering, flowering and yield of agronomic crops and accelerate maturation of cereal crops comprising: applying to said crops plants or to soil containing the seeds other propagating organs of said plants, an effective amount of a compound having the structure:

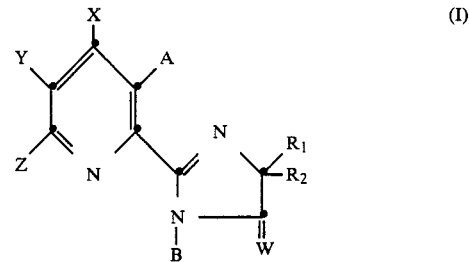

(I)

wherein
$R_1$ is $C_1$–$C_4$ alkyl;
$R_2$ is $C_1$–$C_4$ alkyl or $C_3$–$C_6$ cycloalkyl; and when $R_1$ and $R_2$ are taken together they may represent $C_3$–$C_6$ cycloalkyl optionally substituted with methyl;
A is $COOR_3$, $CONHR_6$, $CHO$, $CH_2OH$, $COCH_3$, $COC_6H_5$, $CN$, $CH_3$, $CH=NOH$, $CH_2COOH$, $CONHOH$, $CH_2CH_2COOH$, $CHR_8OH$,

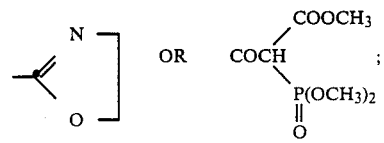

;

$R_3$ is hydrogen,

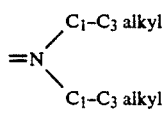

C$_1$–C$_{12}$ alkyl optionally substituted with one of the following groups: C$_1$–C$_3$ alkoxy, halogen, hydroxyl, C$_3$–C$_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium;

C$_3$–C$_{12}$ alkenyl optionally substituted with one of the following groups: C$_1$–C$_3$ alkoxy, phenyl, halogen or loweralkoxycarbonyl or with two C$_1$–C$_3$ alkoxy groups or two halogen groups;

C$_3$–C$_6$ cycloalkyl optionally substituted with one or two C$_1$–C$_3$ alkyl groups;

C$_3$–C$_{10}$ alkynyl optionally substituted with one or two C$_1$–C$_3$ alkyl groups; or, A cation;

R$_6$ is hydrogen, hydroxyl, C$_3$-alkenyl, C$_3$-alkynyl or C$_1$–C$_4$ alkyl optionally substituted with one hydroxyl or one chlorine group;

B is H, COR$_4$ or SO$_2$R$_5$, provided that when B is COR$_4$ or SO$_2$R$_5$; A is COOR$_3$ in which R$_3$ is other than H, or a salt-forming cation, CH$_3$ or CN; W is O and Y and Z are not alkylamino, hydroxyl, or hydroxyloweralkyl;

R$_4$ is C$_1$–C$_{11}$ alkyl, chloromethyl or phenyl optionally substituted with one chloro, one nitro or one methoxy group:

R$_5$ is C$_1$–C$_4$ alkyl or phenyl optionally substituted with one methyl group;

W is O or S;

R$_8$ is C$_1$–C$_4$-alkyl or phenyl;

X is hydrogen, halogen, hydroxyl or methyl, with the proviso that when Y and Z are taken together to form a ring and YZ is represented by the structure: —(CH$_2$)$_n$—, where n is 3 or 4, X is hydrogen;

Y and Z each represent members selected from the group consisting of hydrogen, halogen, C$_1$–C$_6$ alkyl, hydroxy-loweralkyl, C$_1$–C$_6$ alkoxy, C$_1$–C$_4$ alkylthio, phenoxy, C$_1$–C$_4$-haloalkyl, nitro, cyano, C$_1$–C$_4$ alkylamino, diloweralkylamino or C$_1$–C$_4$ alkylsulfonyl group, or phenyl optionally substituted with one C$_1$–C$_4$ alkyl, C$_1$–C$_4$ alkoxy or halogen; and, when taken together, Y and Z may form a ring in which YZ are represented by the structure: —(CH$_2$)$_n$—, where n is an integer selected from 3 and 4, provided that X is hydrogen;

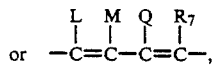

where L, M, Q and R$_7$ each represent members selected from the group consisting of hydrogen, halogen, C$_1$C$_4$ alkyl, C$_1$C$_4$ alkoxy, C$_1$–C$_4$ alkylthio, C$_1$–C$_4$ alkylsulfonyl, C$_1$–C$_4$ haloalkyl, NO$_2$, CN, phenyl, phenoxy, amino, C$_1$–C$_4$ alkylamino, diloweralkylamino, chlorophenyl, methylphenyl, or phenoxy substituted with one Cl, CF$_3$, NO$_2$ or CH$_3$ group, with the proviso that only one of L, M, Q or R$_7$, may represent a substituent other than hydrogen, halogen, C$_1$–C$_4$ alkyl or C$_1$–C$_4$-alkoxy.

and when W is O and A is CN, CH$_3$ or COOR$_3$, provided that R$_3$ cannot be unsaturated alkyl and Y and Z cannot be alkylamino, dialkylamino or alkylthio, and the N-oxides thereof, and when R$_1$ and R$_2$ are not the same, the optical isomers thereof, and, except when R$_3$ is a salt-forming cation, the acid addition salts thereof.

2. The method according to claim 1, to induce tillering, accelerate the maturation and increase the yield of cereal crops comprising: applying to said plants or to the soil containing seeds thereof from 0.0001 kg/ha to 0.01 kg/ha of a compound of claim 1.

3. The method according to claim 1, to induce axillary branching, tillering and to increase the flowering, pod set and yield of legumes comprising: applying to said plants or to soil containing the seeds thereof from 0.0001 kg/ha to 0.01 kg/ha of a compound of claim 1.

4. A method according to claim 1, to increase yield of cotton comprising: applying to said cotton plants or to the soil containing seeds thereof from about 1 g/ha to 380 g/ha of a compound of claim 1.

5. A method according to claim 1, wherein said compound has the structure:

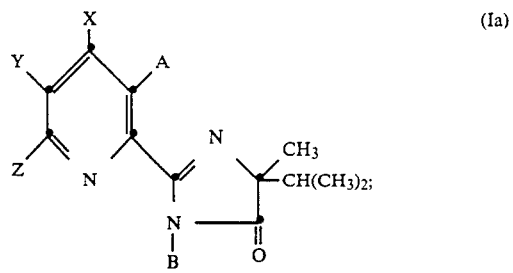

(Ia)

wherein B is hydrogen, CO-alkyl C$_1$–C$_6$ or CO-phenyl; A is COOR$_3$ where R$_3$ is as described in formula (I) above; except that when R$_3$ is a cation, it is a cation of alkali metals, alkaline earth metals, manganese, copper, iron, zinc, cobalt, lead, silver, nickel, ammonium and organic ammonium; X is hydrogen, and Y and Z each represent hydrogen, C$_1$–C$_6$ alkyl, C$_1$–C$_4$-alkoxy, halo, C$_1$–C$_4$-haloalkyl, or phenyl and, when taken together, YZ represent —(CH$_2$)$_4$—.

6. A method according to claim 1, wherein said compound has the structure:

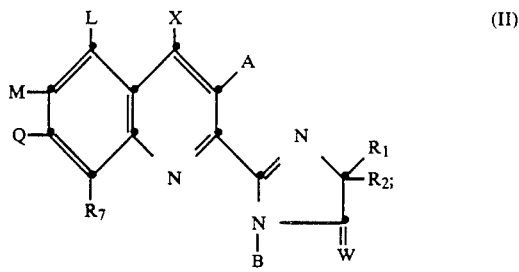

(II)

wherein R$_1$, R$_2$, W, B, A, X, L, M, Q and R$_7$ are as defined in reference to formula (I) above, but especially those wherein R$_1$ is methyl; R$_2$ is methyl, ethyl, isopropyl or cyclopropyl; W is oxygen; B is hydrogen, CO-alkyl C$_1$–C$_6$, CO-phenyl optionally substituted with one chloro, nitro or methoxy group; A is COOR$_3$, CH$_2$OH or CHO; R$_3$ is as defined in formula (I); except that when R$_3$ is a cation, it is a cation of alkali metals, alkaline earth metals, manganese, copper, iron, zinc, cobalt, lead, silver, nickel, ammonium and organic ammonium;

X is hydrogen and L, M, Q and $R_7$ are each selected from the group consisting of hydrogen, halogen, methoxy, nitro, alkyl $C_1$-$C_4$, $CF_3$, CN, $N(CH_3)_2$, $NH_2$, $SCH_3$, or $SO_2CH_3$, provided that only one of L, M, Q or $R_7$ may be nitro, $CF_3$, CN, $N(CH_3)_2$, $NH_2$, $SCH_3$ or $SO_2CH_3$.

7. The method according to claim 2, wherein said cereal crops are barley, oats, rice, rye, wheat and corn.

8. The method according to claim 3, wherein said legumes are soybeans, beans, peas and lentils.

9. A method to regulate growth activity on cereal grains, cotton, soybeans and sugarcane comprising; applying to said crops or to soil containing the seeds or other propagating organs of said crops, an effective amount of a compound having the structure:

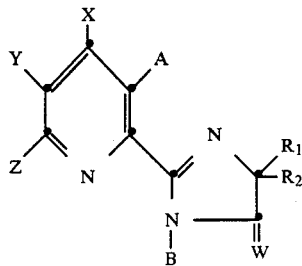
(I)

wherein $R_1$ is $C_1$-$C_4$ alkyl;

$R_2$ is $C_1$-$C_4$ alkyl or $C_3$-$C_6$ cycloalkyl; and when $R_1$ and $R_2$ are taken together they may represent $C_3$-$C_6$ cycloalkyl optionally substituted with methyl;

A is $COOR_3$, $CONHR_6$, CHO, $CH_2OH$, $COCH_3$, $COC_6H_5$, CN, $CH_3$, CH=NOH, $CH_2COOH$, CONHOH, $CH_2CH_2COOH$, $CHR_8OH$,

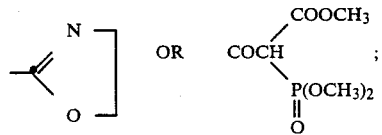

$R_3$ is hydrogen,

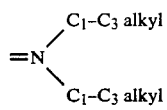

$C_1$-$C_{12}$ alkyl optionally substituted with one of the following groups: $C_1$-$C_3$ alkoxy, halogen, hydroxyl, $C_3$-$C_6$ cycloalkyl, benzyloxy, furyl, phenyl, halophenyl, loweralkylphenyl, loweralkoxyphenyl, nitrophenyl, carboxyl, loweralkoxycarbonyl, cyano or triloweralkylammonium;

$C_3$-$C_{12}$ alkenyl optionally substituted with one of the following groups: $C_1$-$C_3$ alkoxy, phenyl, halogen or loweralkoxycarbonyl or with two $C_1$-$C_3$ alkoxy groups or two halogen groups;

$C_3$-$C_6$ cycloalkyl optionally substituted with one or two $C_1$-$C_3$ alkyl groups;

$C_3$-$C_{10}$ alkynyl optionally substituted with one or two $C_1$-$C_3$ alkyl groups; or, A cation;

$R_6$ is hydrogen, hydroxyl, $C_3$-alkenyl, $C_3$-alkynyl or $C_1$-$C_4$ alkyl optionally substituted with one hydroxyl or one chlorine group;

B is H, $COR_4$ or $SO_2R_5$, provided that when B is $COR_4$ or $SO_2R_5$; A is $COOR_3$ in which $R_3$ is other than H, or a salt-forming cation, $CH_3$ or CN; W is O; and Y and Z are not alkylamino, hydroxyl, or hydroxyloweralkyl;

$R_4$ is $C_1$-$C_{11}$ alkyl, chloromethyl or phenyl optionally substituted with one chloro, one nitro or one methoxy group;

$R_5$ is $C_1$-$C_4$ alkyl or phenyl optionally substituted with one methyl group;

W is O or S;

$R_8$ is $C_1$-$C_4$-alkyl or phenyl;

X is hydrogen, halogen, hydroxyl or methyl, with the proviso that when Y and Z are taken together to form a ring and YZ is represented by the structure: —$(CH_2)_n$—, where n is 3 or 4, X is hydrogen;

Y and Z each represent members selected from the group consisting of hydrogen, halogen, $C_1$-$C_6$ alkyl, hydroxy-loweralkyl, $C_1$-$C_6$ alkoxy, $C_1$-$C_4$ alkylthio, phenoxy, $C_1$-$C_4$-haloalkyl, nitro, cyano, $C_1$-$C_4$ alkylamino, diloweralkylamino or $C_1$-$C_4$ alkylsulfonyl group, or phenyl optionally substituted with one $C_1$-$C_4$ alkyl, $C_1$-$C_4$ alkoxy or halogen; and, when taken together, Y and Z may form a ring in which YZ are represented by the structure: —$(CH_2)_n$—, where n is an integer selected from 3 and 4, provided that X is hydrogen;

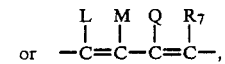

where L, M, Q and $R_7$ each represent members selected from the group consisting of hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $C_1$-$C_4$ alkylamino, diloweralkylamino, chlorophenyl, methylphenyl, or phenoxy substituted with one Cl, $CF_3$, $NO_2$ or $CH_3$ group, with the proviso that only one of L, H, Q or $R_7$, may represent a substituent other than hydrogen, halogen, $C_1$-$C_4$ alkyl or $C_1$-$C_4$-alkoxy.

and when W is O and A is CN, $CH_3$ or $COOR_3$, provided that $R_3$ cannot be unsaturated alkyl and Y and Z cannot be alkylamino, dialkylamino or alkylthio, and the N-oxides thereof, and when $R_1$ and $R_2$ are not the same, the optical isomers thereof, and, except when $R_3$ is a salt-forming cation, the acid addition salts thereof.

* * * * *

UNITED STATES PATENT AND TRADEMARK OFFICE
CERTIFICATE OF CORRECTION

PATENT NO. : 4,957,536
DATED : September 18, 1990
INVENTOR(S) : Philip L. Orwick; Andrew R. Templeton It is certified that error appears in the above-identified patent and that said Letters Patent is hereby corrected as shown below:

In claim 1, Column 22, line 19, "seeds other" should read --seeds or other--.

In claim 9, Column 26, line 51, "H" should read --M--.

Signed and Sealed this

Twenty-eighth Day of April, 1992

Attest:

HARRY F. MANBECK, JR.

*Attesting Officer*  *Commissioner of Patents and Trademarks*